United States Patent
Balazs et al.

[11] Patent Number: 5,669,918
[45] Date of Patent: Sep. 23, 1997

[54] SURGICAL INSTRUMENT FOR PREPARING AN ANASTOMOSIS IN MINIMALLY INVASIVE SURGERY

[75] Inventors: Matthias Balazs, Grafrath; Peter Spitzweck, Inning, both of Germany

[73] Assignee: Deutsche Forschungsanstalt für Luft-und Raumfahrt e.V., Köln, Germany

[21] Appl. No.: 617,170

[22] Filed: Mar. 18, 1996

[30] Foreign Application Priority Data

Mar. 16, 1995 [DE] Germany .................. 195 09 115.9

[51] Int. Cl.⁶ ............................................. A61B 17/00
[52] U.S. Cl. ................... 606/139; 606/148; 606/153; 227/19; 227/176.1; 227/179.1; 227/180.1
[58] Field of Search ............................ 606/139, 142, 606/143, 144, 148, 151, 153, 219, 220; 227/19, 175.1, 176.1, 178.1, 179.1, 180.1, 181.1, 901

[56] References Cited

U.S. PATENT DOCUMENTS

| | | | |
|---|---|---|---|
| 4,593,679 | 6/1986 | Collins. | |
| 4,773,420 | 9/1988 | Green | 227/178.1 |
| 5,389,098 | 2/1995 | Tsuruta et al. | 606/142 |
| 5,433,721 | 7/1995 | Hooven et al. | 606/142 |
| 5,484,451 | 1/1996 | Akopov et al. | 606/139 |
| 5,490,856 | 2/1996 | Person et al. | 606/139 |
| 5,571,117 | 11/1996 | Ahn | 606/139 |

OTHER PUBLICATIONS

German Patent Abstract (DE 3818983), Jun. 3, 1988.
German Patent Abstract (DE 3106490), Feb. 21, 1981.

*Primary Examiner*—Jeffrey A. Schmidt
*Attorney, Agent, or Firm*—Browdy and Neimark

[57] ABSTRACT

Figure 1:
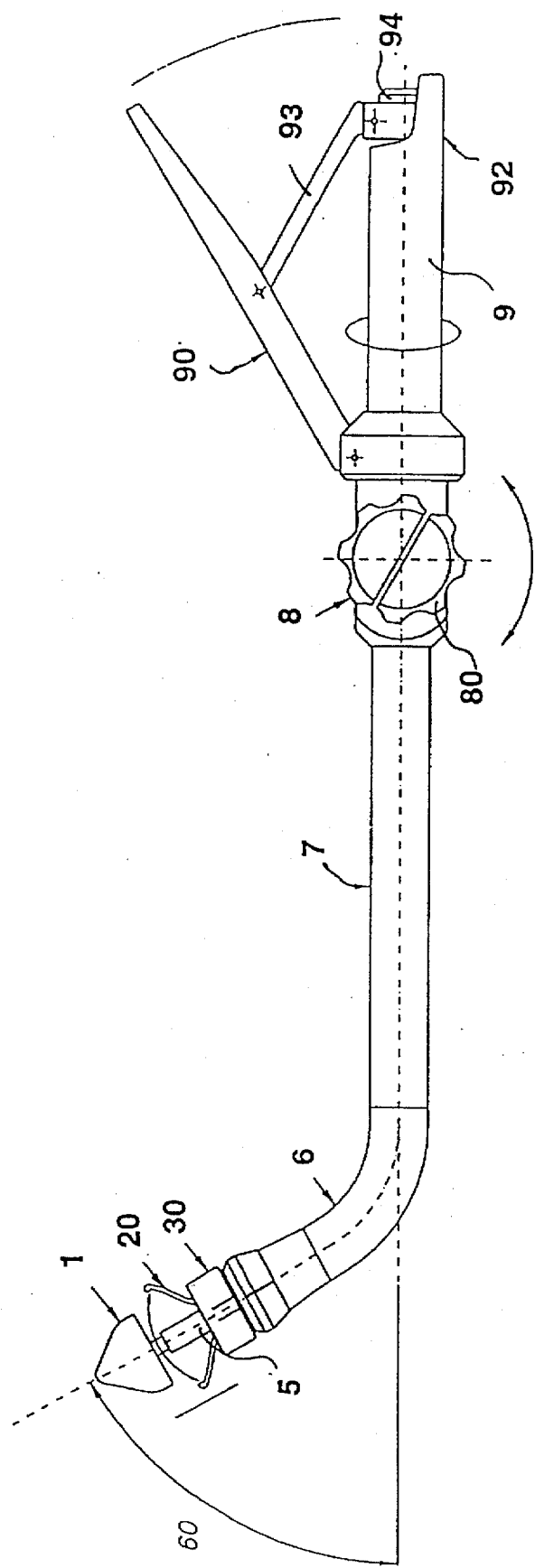

A surgical instrument for one-handed preparation of an anastomosis in minimally invasive surgery has, from the distal end to the proximal end, an interchangeable insertion head (1), a staple holder (30) with U-shaped staples and with a circular groove with thread placed in it, an ejector unit, an gently bendable, adjustable and fixable joint (6), an annular knife retained on the ejector unit, a hollow-cylindrical holder part that is axially displaceable in the annular knife and has a number of elastically resilient, radially pivotable gripper and holder arms (20), a circular-cylindrical shaft (7) mounted on the proximal end of the joint (6), an adjusting and fixing device (8) with a hand wheel (80) mounted on the proximal end of the hollow shaft, and a handle (9) with a toggle lever mechanism (90, 93) pivotably connected to it. (FIG. 1).

19 Claims, 8 Drawing Sheets

Fig.3d

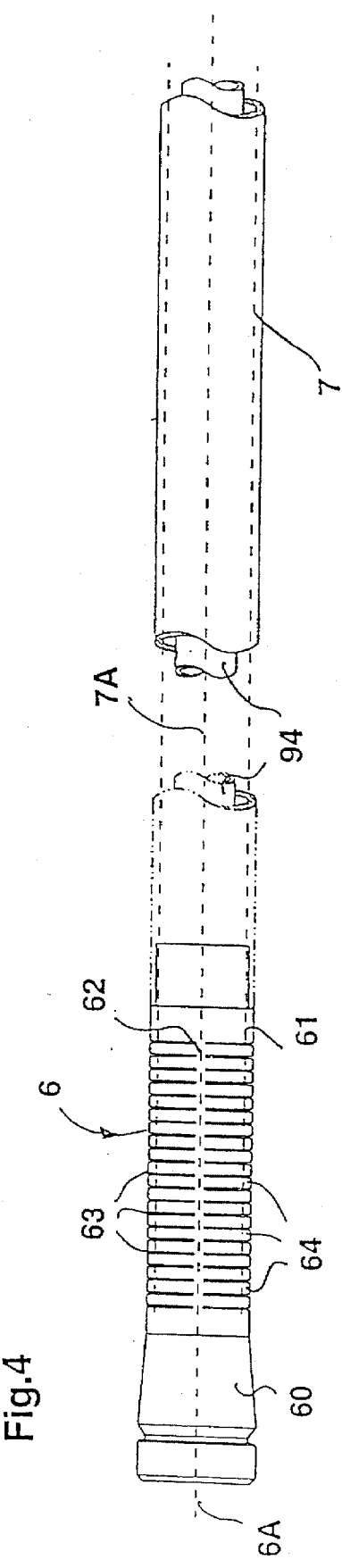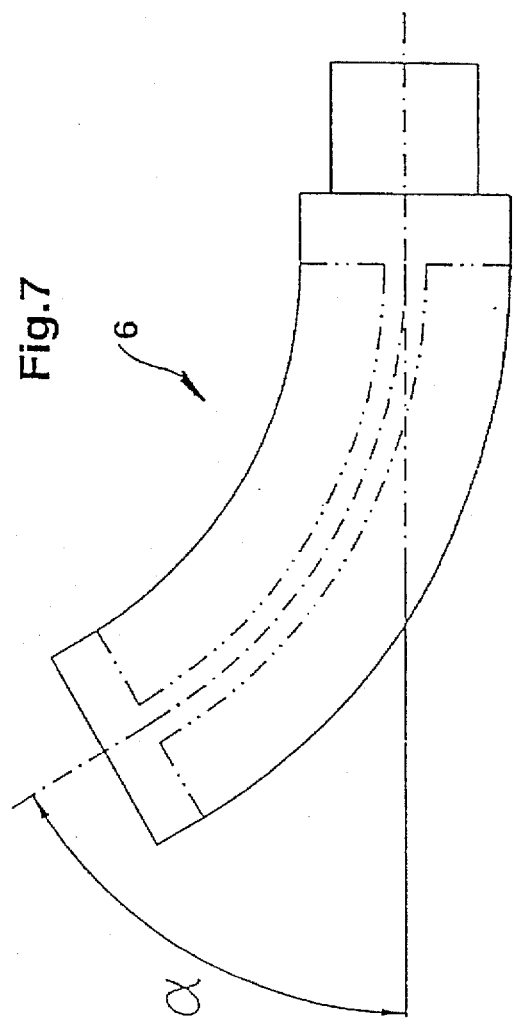

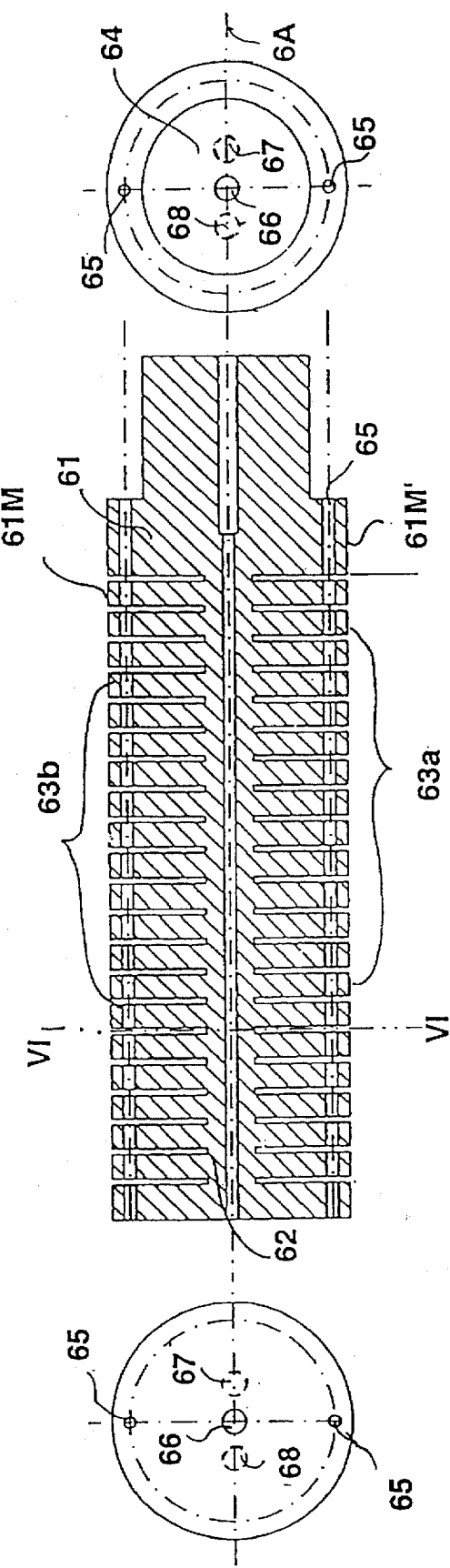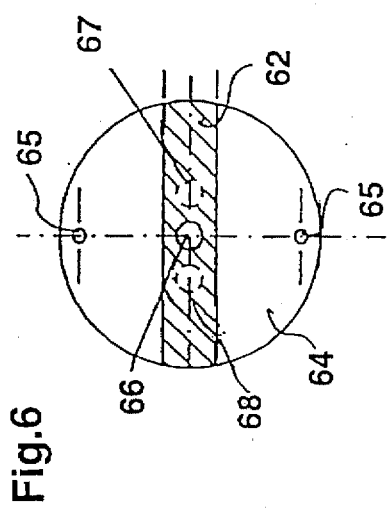

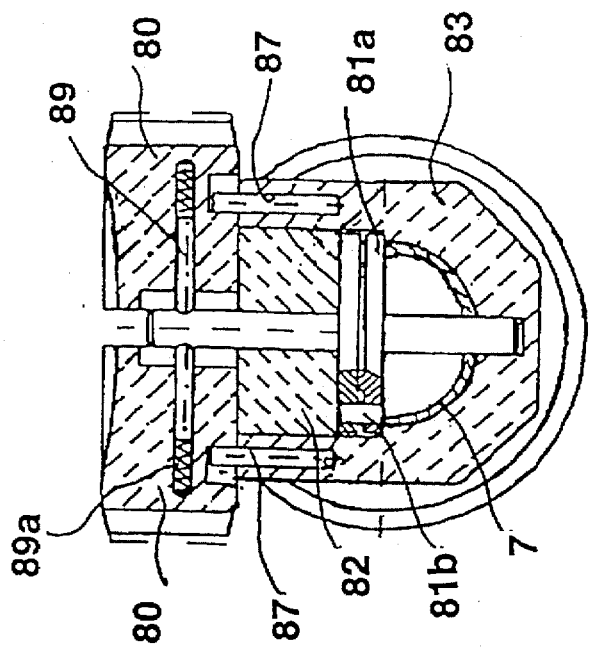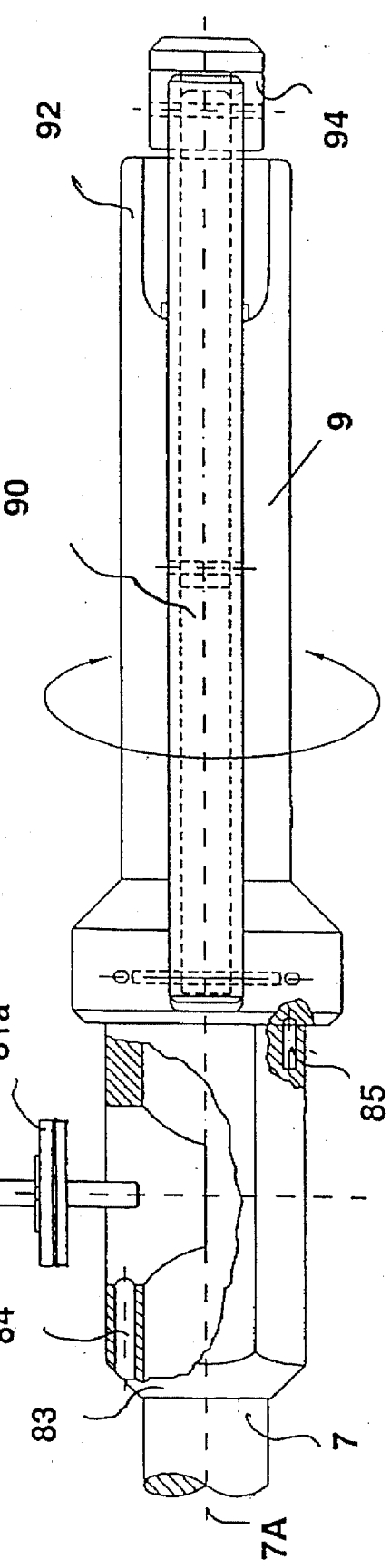

SURGICAL INSTRUMENT FOR PREPARING AN ANASTOMOSIS IN MINIMALLY INVASIVE SURGERY

The invention relates to a surgical instrument for preparing an anastomosis in minimally invasive surgery.

Conventional instruments for the open surgical technique are sewing instruments, in which the two ends of the bowel are threaded onto an instrument head and clamped directly together. This can be done only in the region of the rectum, however, since the sewing equipment must be introduced anally. Also, the known operation procedures can only be done "open", since direct access is necessary to thread the ends of the bowel onto the instrument.

German Patent Application DE 31 06 490 A1, for instance, discloses a surgical stapler for connecting tubular body organs, such as the organs of a digestive tract. This surgical stapler has an elongated body with a tubular housing and a coaxial, cylindrical handle part. A cylindrical staple holder is provided on the free end of the tubular housing and which includes at least one and preferably two rows of surgical staples arranged in a tangential direction. Opposite the cylindrical staple holder in the known surgical instrument, there is a disconnectably retained anvil, in whose face toward the staple holder pairs of pockets corresponding to the tangentially arranged staples are provided for deforming or in other words folding over the free end of staples.

An adjusting head is provided on the free end of the handle part of the instrument body, and by means of this head, with the interposition of an adjusting rod, the anvil can be displaced axially relative to the instrument body from a position in which the anvil is adjacent to the staple holder to a position in which the anvil is at a certain distance from the staple holder. A display unit is also connected to the adjusting head and displays both visually and tangibly when the anvil is positioned at a suitable distance from the staple holder. For precise adjustment of the spacing between the anvil and the staple holder, an annular scale is mounted on the adjusting head.

The known instrument is also provided with a staple driver actuatable from outside by a lever and with a circular-cylindrical scalpel with which parts that after stapling protrude past the end of the bowel can be removed. First of all, the known stapler is an instrument that is used only once, and so only a single stapling operation is performed with it.

As already noted at the outset, conventional surgical instruments are often designed to be introduced only anally and are therefore provided with a rigid, sometimes curved shaft or a slightly bent shaft, which is approximately adapted to the shape of the rectum.

Conventional instruments are also often joined via so-called motion threads, cam disks with teeth, or with a kind of engagement mandrel, to a push rod that is intended to transmit motion to the head of the instrument. A pivot or sliding joint is also coupled to the handle of such a conventional instrument. Quite often, a combination of two different types of drive for controlling the motion of the head part is also provided; however, it is disadvantageous that either only a constant transmission ratio is provided for the main function of "closure of the instrument head", or if there is a transmission ratio that is variable over the adjustment range, production becomes extremely expensive.

German Patent Application DE 38 18 983 A1 discloses an anastomosis device, in the form of a staple applying device which has a gently bendable, adjustable and fixable joint whose flexible region is subdivided into a number of segments, and to the stiff end portion of which an ejector unit is secured. An actuating element is also secured to the proximal end of a plunger, and an insertion head in the form of a cone with a rounded tip is secured to the distal end thereof. The known staple applying device also has a toggle lever mechanism for the final stapling.

U.S. Pat. No. 4,593,679 also discloses an adjusting and fixing device for endoscopes that has two handwheels one above the other for moving and fixing the endoscope.

For inserting bioabsorbent anastomosis rings, so-called purse string sutures must be used, by the aid of which the free edges of two cut bowel ends can be tightened such that they can firmly engage and surround the anastomosis ring.

In open surgery, the purse string suture is either done by hand in the form of simple edge stitching, or so-called purse string staples are used with whose aid the purse string stitching can be done by machine. Occasionally, so-called comb staples are also used for this purpose.

Under what so far are still quite complicated and technologically complex conditions of minimally invasive surgical technique or laparoscopic surgery, however, such purse string staples could not until now be used. Also, no staple suturing devices that can be used in laparoscopic surgery have yet been on the market.

According to the invention, the object is therefore to create a surgical instrument for preparing an anastomosis, with which with a minimally invasive surgical technique, the so-called MIS technique, steps can be carried out for preparing, producing and applying a purse string suture. According to the invention, this is attained in a surgical instrument for preparing an anastomosis in minimally invasive surgery by the characteristics of claim 1. Advantageous further features are the subject of claims dependent directly or indirectly on claim 1.

The surgical instrument according to the invention serves preferentially to prepare severed bowel ends for rejoining of bowel anastomoses by minimally invasive surgery. With the surgical instrument according to the invention, various functions can be performed, namely fixing of the bowel end, application of a loop of thread, stapling the thread loop as a purse string suture to one bowel end, and finally cutting off of the bowel end all the way around.

Also in the surgical instrument of the invention, improved freedom of motion is obtained because an gently bendable joint is provided. In this connection, the term "gently bendable" is understood to mean bending via a certain predetermined radius, unlike kinking at one point. Since the surgical instrument according to the invention is contemplated for use in minimally invasive surgery, the instrument is placed in the actual operation field within a retrieval trocar introduced through small incisions into the abdominal wall of a patient.

When the technique of minimally invasive surgery is used, the patient is therefore under substantially less intraoperative stress, for one thing, and for another, healing after the operation is considerably faster, so that with a considerably shorter hospital stay, the expenses can be reduced considerably. With the surgical instrument according to the invention it is possible for the surgeon to perform anastomosis by minimally invasive surgery, since all the steps in the operation can be laparoscopically in the abdomen by way of retrieval trocars, and thus direct access as in the open surgical technique is not longer necessary.

To suitably prepare the severed bowel ends so that a bowel anastomosis can be done, the steps listed above are carried out one after the other. To that end, the surgical instrument according to the invention has the following essential elements or structural groups:

For inserting the instrument head into a free bowel end, an interchangeable insertion head is provided which has soft contours and rounded transitions and is thus atraumatic in its overall design. In the preferably circular underside of the insertion head, radially arranged staple bending indentations are provided.

In a circular-annular staple holder, conventional U-shaped staples are arranged in the radial direction, matching the staple bending indentations provided in the underside of the insertion head, and are oriented relative to these indentations. Arranging the fixation staples radially is especially advantageous, because when the instrument head is retracted from the bowel end, the circumferential expansibility of the bowel is in no way restricted by the staples applied, and thus the bowel is protected against any injuries.

To enable fixing a bowel end onto an anastomosis ring, when a Valtrac® or bioabsorbable anastomosis ring is used, a purse string suture is generally employed. Such a purse string suture can be applied by the surgical instrument of the invention. To that end, the bowel is drawn over the instrument head, in the form of the insertion head, and secured by means of gripper and holder arms against unintended slipping off of the insertion head in the following manner.

For catching and fixing a bowel end on the insertion head of the instrument, a number of elastically resilient, radially pivotable gripper and holder arms are provided, which are accommodated in an axially displaceable holder part and are preferably made of dirt-repellent elastic Teflon®. Especially through hooklike shoulders protruding inward from the distal ends of the gripper and holder arms, the respective bowel end is fixed to the insertion head and is thereby prevented from slipping off during the ensuing stapling, suture application and excision.

The staple holder, acting as a kind of staple magazine, an annular knife with a circular-linear blade, and an ejector unit that is retained displaceably relative to the staple holder, can be resupplied, if need be even during an operation, for example outside the body between two insertions of the surgical instrument. In the surgical instrument according to the invention, it is possible at any time for an instrument to be used multiple times during one operation.

After thorough cleaning and sterilization, the instrument of the invention can be re-employed and inserted again at any time. This is made possible, in the surgical instrument of the invention, because first, it has the above- listed, quickly and easily interchangeable elements, so that even during an operation the instrument can be re-equipped with various parts, and second, by the provision of suitable flushing conduits for post-operative cleaning and sterilization, it is designed to be extraordinarily easy to clean.

The insertion head acting as the head of the instrument can be replaced quickly and easily, as already noted, so that the surgical instrument according to the invention can be adapted to the various sizes of the bowel, such as the large intestine, small intestine, and duodenum, by using insertion heads of different head diameters. By using an insertion head whose head diameter is adapted to the various bowel sizes, it is assured that traumatic injuries to the adjacent tissue will not occur. Because of the advantageous embodiment of the surgical instrument of the invention, the various functional groups thereof are used repeatedly, in accordance with their respective length of service life, and as wear parts can be removed and replaced independently of one another. For instance, the annular knife provided according to the invention with a circular-linear blade can be embodied as a re-sharpenable component. The staple holder acting as a staple magazine is equipped with staples, packed in sterile form, and designed as a replacement unit.

In the staple holder used according to the invention, in which as already noted the various staples are arranged radially, a circular groove is also provided in the free interior of the staples, and a thread in the form of a thread loop is placed in the groove. In the surgical instrument of the invention, a thread loop is thus secured to the bowel by means of staples. Moreover, practically simultaneously with the application of the staples to the respective bowel end and the placement of the thread loop, excess protruding bowel is cut off by means of the annular blade.

As already noted, the freedom of motion in the abdomen is increased by the gently bendable joint, which is especially important and advantageous in the technique of minimally invasive surgery, because despite limited space conditions, good accessability to the ends of the bowel is assured.

In a preferred embodiment of the invention, the gently bendable joint in the surgical instrument is therefore provided directly on the proximal end of te actual instrument head, which is substantially formed by the insertion head, the staple holder with thread guidance, the ejector unit, and the annular blade. Moreover, because of the "gentle bending form" of the joint, which above all has a smooth outer form without any corners, protrusions or edges whatever, atraumatic use in the operation field, especially in the abdomen, is assured. Preferably, the joint also performs additional mechanical functions; for instance, a driving mechanism for the instrument head is guided in the joint.

The driving mechanism for the instrument head is provided in and on a straight circular-cylindrical hollow shaft that is secured to the proximal end of the joint. Such a circular-cylindrical hollow shaft in laparoscopic instruments has proven itself in the technique of minimally invasive surgery and in the embodiment according to the invention it also enables axial movement of the surgical instrument within the retrieval trocar. A straight hollow shaft is also advantageously guidable.

In the surgical instrument of the invention, the two possibilities of motion, namely simply guiding the hollow shaft in the axial direction and rotation about the longitudinal axis, are expanded by the gently bendable head and by a certain play in the retrieval trocar. The play in the retrieval trocar is relatively slight. However, the trocar is located in the abdominal wall, which in an operation is "blown up" with gas and which thus, being a flexible membrane, allows tilting in the insertion region. The play in the retrieval trocar depends on the shaft diameter, which however can be chosen to be smaller than the diameter of the insertion head.

In the hollow shaft, along with a transmission member for opening and closing the elements accommodated on the distal end of the instrument for applying the loop of yarn, applying the staples, fixing the bowel and cutting off any protruding bowel, there are also actuation elements for bending and fixing the instrument head, which can be done completely independently of the above, in any arbitrary position between 0° (which corresponds to the elongated, straight basic position) and bending of approximately 60°, for instance.

Preferably used bendable surgical elements are nearly always "flexible" and therefore deflect in response to mechanical strains. Therefore if relatively high forces must be transmitted, of the kind that occur when a protruding bowel end is cut off, for instance, then a fixedly adjustable joint of the kind provided in the surgical instrument of the invention is indispensible.

In the preferred embodiment according to the invention, the gently bendable joint is distinguished in particular in that it has a mechanical end stop, which in terms of rigidity is comparable to a rigidly bent element.

Moreover, prestressing is possible in the invention, so that the joint can be fixed in arbitrary intermediate positions, with relatively slight sacrifices in terms of its rigidity. To that end, in a preferred embodiment of the invention, an adjusting and clamping wheel is provided, with which the "clamping" funktion is performed automatically by means of spring prestressing.

Also in the version of the adjusting and clamping wheel according to the invention, an adjustment of the bending—with brief suspension of the clamping—is made possible merely by pressing together the handle halves of the two-part adjusting and clamping wheel. The handle is also designed ergonomically and has a dividing plane by which a surgeon is provided with a display outside the body of the angular position of the instrument head at a given time.

Moreover, on the proximal end of the hollow shaft remote from the joint, a handle that is freely rotatable about the longitudinal axis of the shaft is provided, on which according to the invention a toggle lever mechanism is provided. When it is actuated, the main functions of the surgical instrument of the invention upon closure of the instrument head can be carried out by bringing the insertion head to the staple holder, acting as an anvil, opposite it; these functions are namely retention of the bowel end by the gripper arms and, by exerting slight pressure on the insertion head, applying the thread loop when the fixation staples are applied, and cutting the protruding bowel end off all the way around. The toggle lever mechanism is also advantageously designed such that it opens again automatically after being released.

Moreover, in the toggle lever mechanism its transmission ratios are adapted to the requisite course of motion of the functional elements in the instrument head, especially of the gripper and holder arms, annular knife and staple ejector unit. Thus it is especially advantageous in the preferred embodiment of the instrument according to the invention that with the aid of the toggle lever mechanism pivotably connected to the handle, all the above-discussed functions of the instrument head can be triggered with one hand and performed by the instrument head.

Despite or precisely because of this ease of use, however, both the manufacture and the assurance of the various functions of the surgical instrument can be assured more easily and more reliably than in most previously known surgical instruments. Above all, as already noted at the outset, comfortable, convenient operation is assured, because it is for instance assured by means of a spring that after actuation and the ensuing release of the toggle lever mechanism, this mechanism automatically opens again.

Unlike previously known conventional instruments, which are designed for only a single use, the surgical instrument of the invention is designed for repeated use, as already noted above. Naturally in that case not only convenient and complete sterilizability but also perfect, complete cleaning of all the components of the surgical instrument must be assured, which is also actually achieved by making suitable structural provisions, in terms of shaping and the mode of operation.

With respect to the materials used for the various elements, in particular, more-stringent demands must be met, because it is taken into account for instance which elements must be handled constantly with aggressive chemical cleaners, which must be capable of withstanding flushing pressure, and which must not vary their properties, such as their shape and mechanical strength, surface quality and moisture absorption, in steam sterilization under pressure and at temperatures above 130° C.

Taking these aspects into account, all the heavily stressed components, such as the hollow shaft, driving mechanism, actuating wire, tension wires, connecting elements, shafts, the annular knife, and the like are therefore preferably all made of high-alloy stainless steel, preferably X40Cr13. All the parts that undergo bending stress, such as the bendable joint, the holder part with the gripper and holder arms and the like, are made of a soft elastic, extremely tough plastic; because of its medical comparability combined with its dirt-repellent material structure, polytetrafluoroethylene (PTFE) is preferably used. For other parts, such as the insertion head, the staple holder, the mandrel, the handle, and the hand wheel provided on the shaft, parts which generally are not subjected to major deformation, harder plastic is used, preferably polyoxymethylene (POM).

Figure 2A:
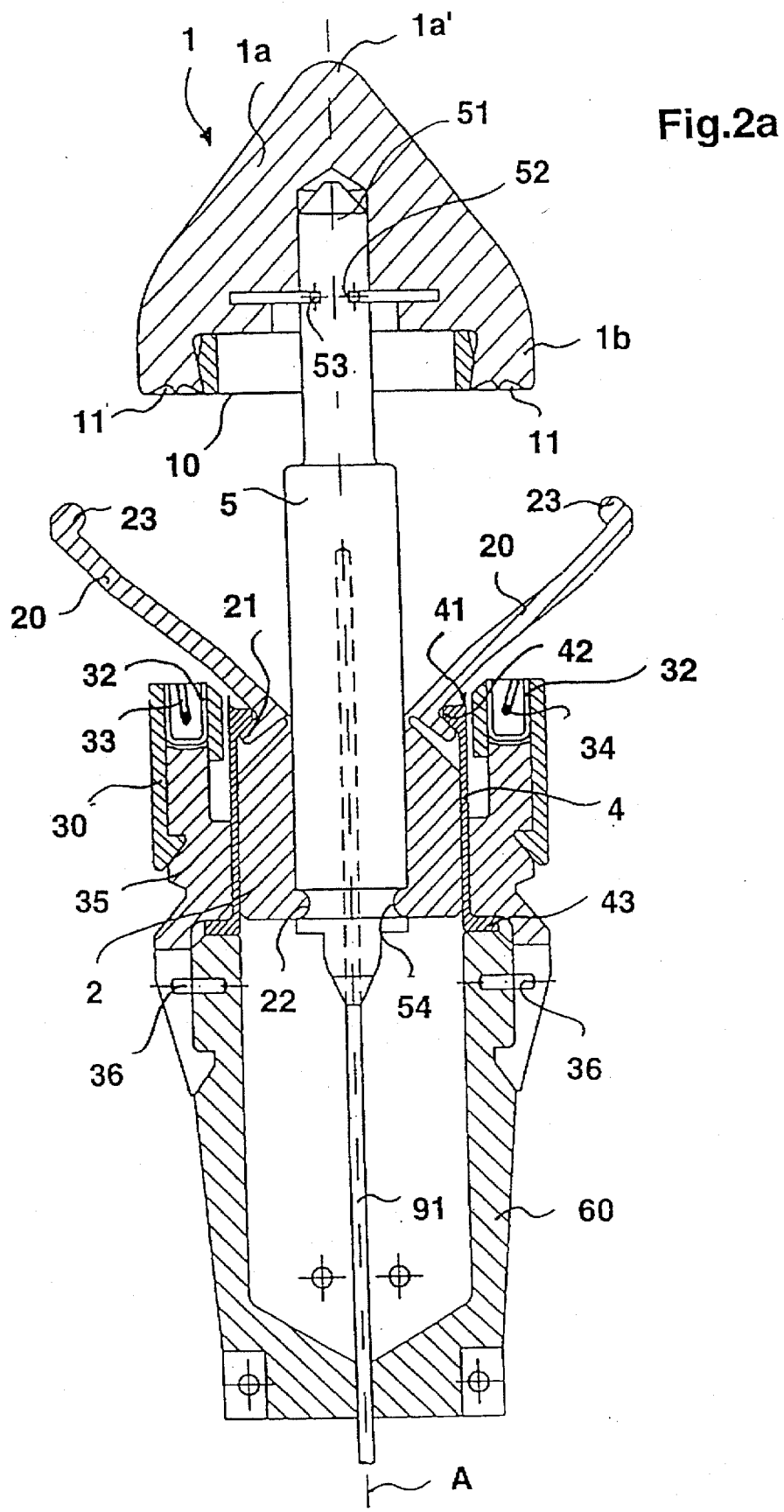
Figure 2B:
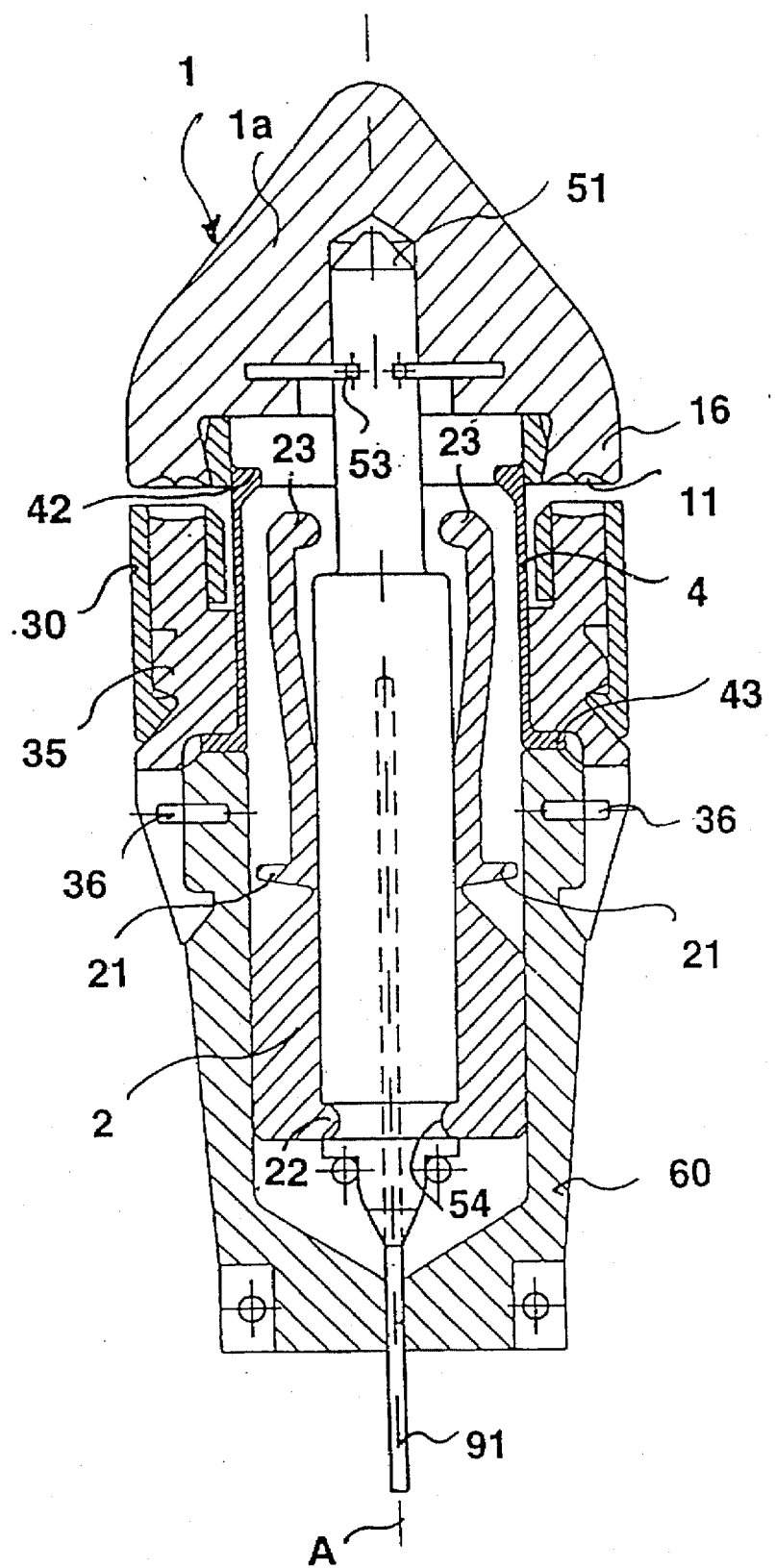
Figure 9:
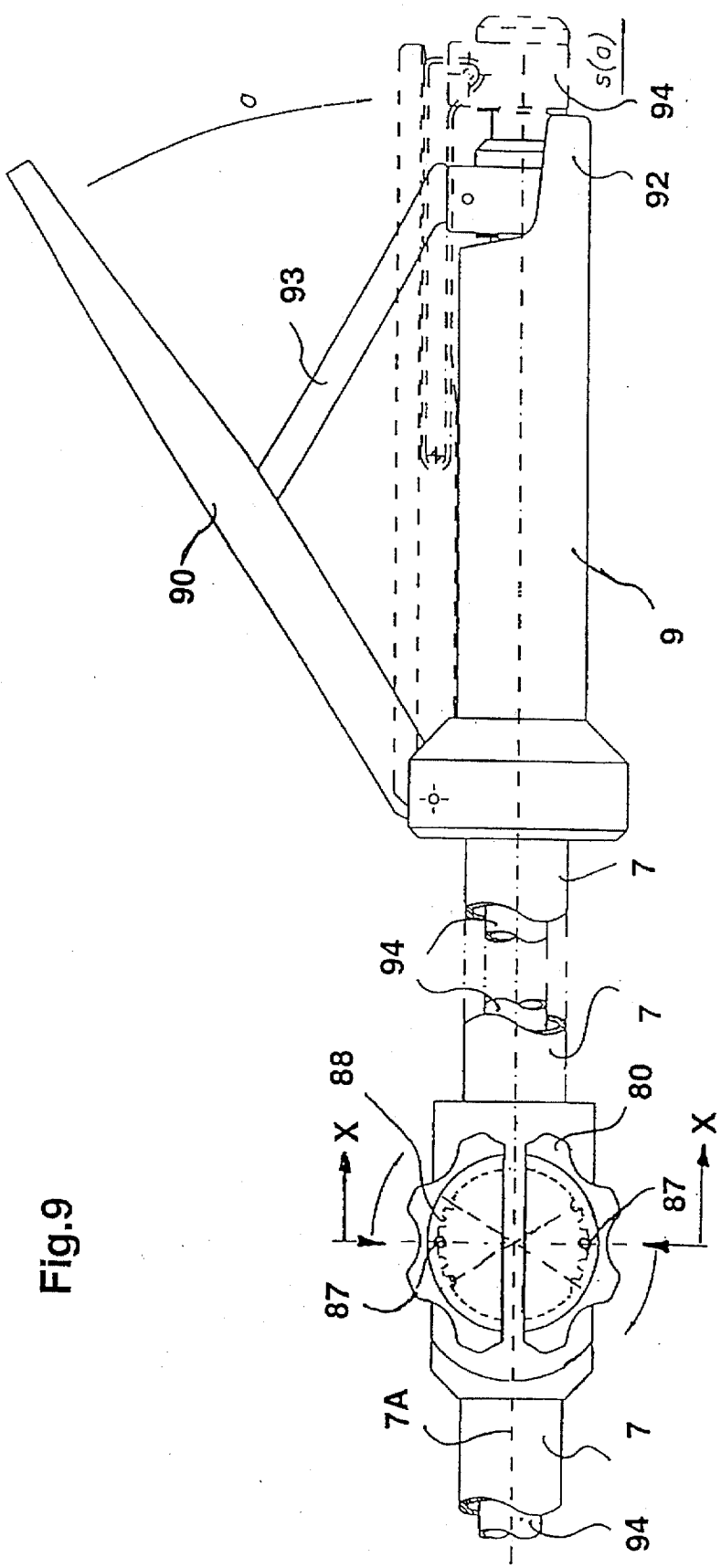

The invention will be described in detail below in terms of preferred embodiments, in conjunction with the accompanying drawings. Shown are:

FIG. 1, in plan view, a schematic illustration of an entire surgical instrument of the invention in the bent state;

FIG. 2a, in a sectional view, functional elements provided on the distal end of the surgical instrument of FIG. 1, shown in their open state;

FIG. 2b, the functional elements of FIG. 2a, provided on the distal end of the surgical instrument, in the closed state;

FIGS. 3a–3f, in sectional views, plan views and partly in enlarged details, individual views of the various functional elements shown in the mounted state in FIGS. 2a and 2b;

FIG. 4, in schematic plan view, a joint shown drawn out and, partly in a perspective sectional view, a hollow shaft mounted on the proximal end of the joint;

FIG. 5a, a plan view of the distal end of a joint;

FIG. 5b, a longitudinal sectional view of the main part of the joint;

FIG. 5c, a plan view of the proximal end of the joint;

FIG. 6, a sectional view taken along a line VI—VI of FIG. 5b;

FIG. 7, a schematic view of a joint of FIGS. 5a–5c in the bent state;

FIG. 8, a side view of a schematic illustration, shown partly in section and partly separated into individual parts, of an adjusting and fixing device, and a plan view of a handle with a toggle lever mechanism mounted on the distal end of the adjusting and fixing device;

FIG. 9, a plan view of the adjusting and fixing device shown in FIG. 8 in a side, and a side view of the handle with the toggle lever mechanism pivotably connected to it; and FIG. 10, a sectional view of the adjusting and fixing device along a line X—X of FIG. 9.

The views shown in FIGS. 1–10 are not to scale and are some of them on different scales.

In FIG. 1, in a preferred embodiment, a complete view of a surgical instrument of the invention is shown in the bent state; of the instrument serving as an applicator, the elements schematically shown, in order from its distal end to its proximal end, are an insertion head 1, gripper and holder arms 20 that are pivotable radially outward from a holder part, a circular-cylindrical mandrel 5, a staple holder 30, a joint 6 bent at an angle of about 60°, a hollow shaft 7, an adjusting and fixing device 8 with a hand wheel 80 split into two parts, and a handle 9 with a toggle lever mechanism 90, 91 pivotably connected to it. A center line of the surgical instrument is also suggested in dashed lines in FIG. 1.

Figure 3A:
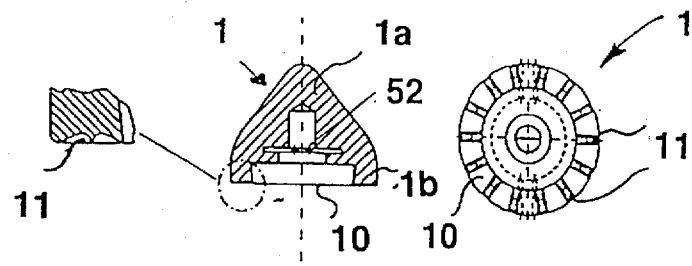
Figure 3B:
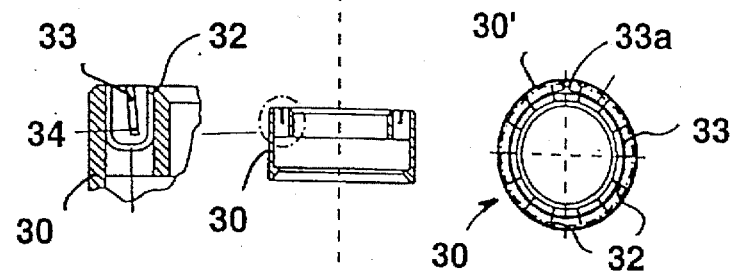
Figure 3C:
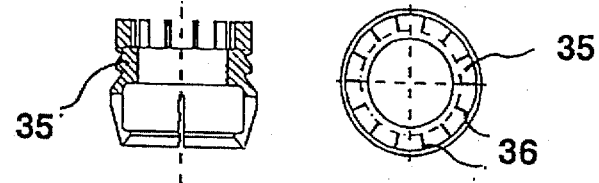
Figure 3E:
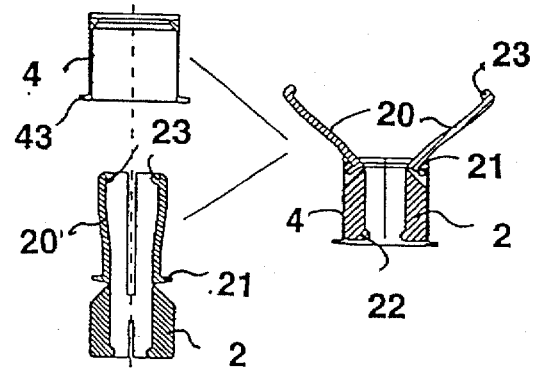
Figure 3F:
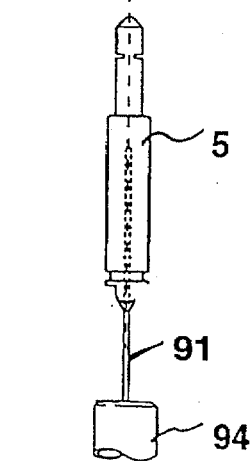

As can be seen from the sectional views in FIGS. 2a and 2b and in a sectional view, plan view and enlarged individual view in FIG. 3a, the insertion head 1 has a cone 1a in its upper portion, with a rounded upper end 1a', and a circular-annular shoulder 1b. In the circular-annular underside 10 of the insertion head 1, radially oriented staple indentations 11 are formed, as can be seen in an enlarged detail view in the left-hand portion of FIG. 3a and in a view from below in the right-hand portion of FIG. 3a. Suitably dimensioned recesses (not shown) for receiving the mandrel 5, which terminates in a truncated cone 51, are provided symmetrically to a center axis represented by the dashed line in FIGS. 2a, 2b and 3a.

The insertion head 1 is embodied as a part that can be replaced quickly and easily. This has the advantage that insertion heads with different head diameters can be kept in readiness and matched to the various possible bowel diameters, for instance for the large intestine, small intestine, duodenum, and the like. This assures that traumatic injuries to the adjacent tissue will not be caused by the insertion heads.

In FIGS. 2a and 2b, at a suitable distance from the underside 10 of the insertion head, a staple holder 30 which is circular-annular in plan view is shown (see the outer right portion of FIG. 3b), in which receptacles, not identified by reference numeral, for the U-shaped staples 32 oriented and accommodated radially are disposed in such a way that each staple 32 has a bending indentation 11 assigned to it in the underside 10 of the head. A circular-annular groove 33 is provided in the free interior of the staples 32, and as can be seen from the plan view shown on the outer right in FIG. 3b, this groove, at a point marked 33a, intersects the outer circumference 30' of the staple holder 30. As suggested in the view of FIG. 3b, a thread 34 is placed in a loop in the groove 33.

Below the staple holder 30, as can be seen in FIGS. 2a and 2b, an ejector unit 35 is provided, which as suggested in FIG. 1 by an arrow with two heads shown next to the gripper and holder arms 20, is disposed so as to be displaceable parallel to the center line. The two possible terminal positions of the ejector unit 35 are shown in the two sectional views of FIGS. 2a and 2b. As can be seen from the plan view in FIG. 3c, a number of ejector plungers 37 is provided in the upper part of the circular-annular ejector unit 35 to correspond to the number of staples 32 or associated bending indentations 11.

In the interior of the ejector unit 35 and of the staple holder 30, an annular knife 4 is provided, which has a circular-linear blade 41. Directly below the blade 41, the annular knife 4 has a collar 42, of approximately triangular cross section, protruding horizontally into the interior for actuating the gripper and holder arms. On an end of an annular knife 4 remote from the blade 41, the knife has a circular-annular shoulder 43, bent outward by 90°, by means of which shoulder the annular knife 4, as FIGS. 2a and 2b show, is securely held between the ejector unit 35 and an end portion 60 of the joint 6. The ejector unit 35 is secured to the end portion 60 of the joint, for instance by means of bolts or pins 36 schematically suggested in FIGS. 2a and 2b.

In the circular-cylindrical interior of the annular knife 4, a holder part 2 is provided, on whose distal end, that is, the upper end in FIGS. 2a and 2b, a number of elastically resilient gripper and holder arms 20 are provided. Hooklike shoulders 23 are formed on the free end of the gripper and holder arms 20, protruding inward in the direction toward the center axis A of the instrument. In the region of transition from the holder part 2 to the gripper and holder arms 20, radially outward-projecting protrusions 21 are formed on these arms.

On its lower end in FIGS. 2a and 2b, the holder part 2 has a radially inward-protruding annular shoulder 22. A suitably-sized groove 54 in the mandrel 5 corresponds with the annular shoulder 22. A relatively stiff actuating wire 91 is preferably secured on the lower end of the mandrel 5 in FIGS. 2a and 2b.

In FIG. 2b, the holder part 2 is shown retracted into the hollow end portion 60 of the joint. FIG. 2b shows the status of the instrument head after it has been actuated; the staples have been expelled, and the staple holder acting as a magazine has locked into the "open" position on the holder part.

The instrument head, in the state shown in FIG. 2a, is brought to the vicinity of the bowel end to which a purse string suture is to be applied. This bowel end is held for instance by means of forceps inserted through a second trocar. The insertion head is then introduced into the bowel end, held in this way in a predetermined position, with the instrument head "open" as shown in FIG. 2a, so that the bowel end comes to rest between the insertion head 1 and the gripper arms 20.

On retraction of the mandrel 5 from the position shown in FIG. 2a, the gripper and holder arms 20 resiliently held on the distal end of the holder part 2 are pivoted in the direction of the center axis A of the instrument, and with their outward-projecting protrusions 21 they come into contact with the circular-annular collar 42, of triangular cross section, of the annular knife 4.

In this course of motion, the protruding bowel is pressed by the hooklike shoulders 23 of the gripper and holder arms 20 against the plunger 5, thus preventing the bowel end from unintentionally slipping off the insertion head. As soon as the mandrel 5 and hence the insertion head 1 are approximately in this position, the staple holder 30 comes into contact with the fixed bowel end. In the further axial displacement of the mandrel toward the hollow end portion 60 of the joint, the ejector unit 35 is pressed into the position shown in FIG. 2b, and as a result the staples 32 accommodated in the staple holder 30 pierce the fixed bowel end and are deformed in the bending indentations 11 provided on the underside 10 of the head. At the same time, any excess protruding bowel is cut off by means of the circular-linear blade 41 of the annular knife 4.

By the penetration and bending over of the staples 32, a loop of thread is simultaneously applied as well, by means of the thread 34 accommodated in the groove 33; the ends of the thread intersecting at the point 33 protrude beyond the outer circumference 30' of the staple holder 30. In this way, by means of the surgical instrument of the invention, a purse string suture is thus applied to one bowel end, and the bowel end is prepared for receiving a Valtrac® or bioabsorbent anastomosis ring.

Because of the atraumatic design and in particular of the underside 10 of the insertion head 1, the surgical instrument, with whose aid the purse string suture has been applied, can now be retracted from the prepared bowel end. After the insertion of a sterile-packed staple holder equipped with staples, the surgical instrument of the invention can immediately be re-used for preparing a further purse string suture on the other bowel end. FIG. 4 in plan view shows a joint 6 shown in its straight or elongated form; on its distal end, it has the end portion 60 shown in section in FIGS. 2a and 2b. On the proximal end of the joint body 61, the hollow shaft 7 shown partly in a perspective sectional view in FIG. 4 is attached. As shown in FIG. 1, the joint 6 can be bent at an angle of up to 60°.

As can be seen in detail from a longitudinal sectional view in FIG. 5b and the plan views on the distal and proximal end, respectively, of a joint 6 in FIGS. 5a and 5c, the main portion of a joint body 61 comprises a circular-cylindrical block of material, in which a number n of notches 63 has been made. The notches begin at two diametrically opposed jacket lines 61M and 61M' of the cylindrical joint body 61 and are both parallel to and equidistant from one another.

In the preferred embodiment shown in FIG. 5b, the notches 63 are made vertically to the longitudinal axis 6A of the joint, deep enough into the block of material that the (n+1) segments 64 between the individual notches 63 are joined together on their opposing ends by an approximately rectangular, weblike cross-sectional region 62, as can be seen from the sectional view of FIG. 6 takes along a line VI—VI of FIG. 5b.

As shown in the plan views of FIGS. 5a and 5c and the sectional view of FIG. 6, in the outer region of the total of (n+1) segments, preferably diametrically opposed and aligned bores 65 are provided. In the bores 65 aligned with one another, actuating means in the form of tension-exerting means are accommodated, which are permanently joined to the end portion 60 of the joint. With the aid of these actuating means, the joint 6 can be bent out of its elongated starting position (see FIG. 1), which corresponds to an angle of 0° relative to its longitudinal axis 6a, for instance in the plane of the drawing, by an angle of 60°.

As can also be seen from the plan views in FIGS. 5a and 5c and the sectional view of FIG. 6, at least one continuous, closed working conduit 66 is formed symmetrically to the center axis (6A) of the joint. In an advantageous further feature of the joint 6 used in the surgical instrument of the invention, one or two more closed conduits 67 and 68 can be formed if needed in addition to the closed working conduit 66, as suggested by dashed lines in FIG. 5a, 5b and 5c. The optical waveguide required for endoscopy is preferably accommodated in the conduit 66 disposed symmetrically to the center axis of the joint. In FIG. 7, only a joint 6 is schematically shown, bent at an angle α which is generally a maximum of 60°.

The left-hand portion of FIG. 8 shows an adjusting and fixing device 8, separated into its individual parts and shown partly in section. A shaft 81, disposed perpendicular to the longitudinal axis 7A, is rotatably supported in a housing 83, shown partly cutaway, and a grooved disk 81a is joined to this shaft in a manner fixed against relative rotation. For deflection the joint 6, actuating means in the form of tension-exerting means can be secured in prestressed fashion on the grooved disk 81a by means of bolts 81b, as shown in the sectional view of FIG. 10. A bearing shell 82 also has a bore 86 extending parallel to the longitudinal axis 7A, by means of a grub screw (not shown) inserted via a housing bore 85, the shaft 81 is fixed in the bearing shell 82 relative to the housing 83, and at the same time the tension-exerting means are prestressed without play.

In a hand wheel 80 split into two parts (see FIGS. 9 and 10), which is retained on the shaft 81 by a pn 89 and which functions as an adjusting and clamping wheel, the "clamping" function is automatically achieved by prestressing which is operative between the two hand wheel halves and is exerted for instance by helical springs 89a between the pin 89 and the hand wheel halves 80. By compressing the two halves of the hand wheel 80, which is represented in FIG. 9 by two arrows pointing at the hand wheel 80, the clamping is briefly undone, and an adjustment corresponding to the desired bending of the joint 6 can be performed, by rotating the hand wheel 80 far enough in the desired direction that pins 87 secured in the housing 83 lock into recesses 88 provided on the under side of the as suggested by dashed lines in FIG. 9. As can be seen from the plan view of FIG. 9, the two halves of the hand wheel 80 are shaped ergonomically and the dividing plane extending in the middle between the two halves shows the surgeon outside the body how the joint 6 is bent and hence shows the angular position of the instrument.

In the housing 83 of the adjusting and fixing device 8, a fixed pin 85 is also provided, which in an adjoining end face of the handle 9 is assigned a number of indentations, so that the handle 9 together with the toggle lever mechanism 90 pivoted to it can be rotated relative to the adjusting and fixed device 8, as suggested by an elliptical line with two arrow heads.

As already noted at the outset, by means of the toggle lever mechanism pivoted connected to the handle 9, the main function of the surgical instrument of the invention is carried out; specifically, upon closure of the instrument head, the protruding bowel is automatically held and at the same time the fixing staples are inserted, a loop of thread is placed, and in addition the excess bowel is cut off or cut out all the way around. After the toggle lever mechanism 90 is released, its opening occurs automatically; the pressure rod 93 of the toggle lever mechanism 90, which rod is pivotably connected to the proximal end of the transmission member 94, is pressed away from the end portion 92 of the handle by a spring (not shown).

The transmission ratio of the toggle lever mechanism 90 pivotably connected to the handle 9 and transmission member 94 is adapted precisely to the requisite action path s(a) (see the arrow pointing to the right, outward, shown in the extension of the handle 9 in FIG. 9) and to the course of motion of the individual functional elements in the instrument head, especially the gripper and holder arms 20, annular knife 4, and ejector unit 35.

In FIG. 8, the toggle lever mechanism 90 is shown in the actuated state, and from this it can be seen that the proximal end of the transmission member 94 protrudes beyond the handle 9. The same situation is suggested in dashed lines in the plan view of FIG. 9. The pulled-apart toggle lever mechanism 90, 93 in FIG. 9 shows its unactuated state and indicates a position that the toggle lever mechanism 90 automatically assumes under spring action after being released.

We claim:

1. A surgical instrument for preparing an anastomosis by minimally invasive surgery, in which an instrument serving as an applicator and being insertable from the distal end to the proximal end into a retrieval trocar, has the following:

an interchangeable insertion head (1) with radially oriented staple-bending indentations (11);

a staple holder (30) with receptacles for radially oriented U-shaped staples (32) and with a circular groove (33), provided in the free interior thereof, into which groove a thread (34) is placed;

an ejector unit (35), on which the staple holder (30) is retained axially displaceably;

a joint (6) that can be gently bent at an angle and adjusted and fixed, on the stiff end portion (60) of which the ejector unit (35) is secured;

an annular knife (4) with a blade (41) in the form of a circular line, the knife being held between the end portion (60) of the joint and the ejector unit (35);

a hollow-cylindrical holder part (2) that is axially displaceable in the annular knife (4) and the end portion (60) of the joint and that has a number of elastically resilient, radially pivotable gripper and holding arms (20), a mandrel (5), on which for its axial displacement an actuating element (91, 94) is secured and on which the insertion head (1) and gripper arm holder part (2) are disconnectably retained;

a circular-cylindrical hollow shaft (7) mounted on the proximal end of the joint (6);

a handle (9) with a toggle lever mechanical (90, 93) pivotably connected to it, so that with one hand when it is actuated by means of the actuating element (91, 94) the mandrel (5) and thus the gripper arm holder part (2) and the insertion head (1) can be retracted in the direction of the hollow shaft (7), as a result of which the staples (32) are ejected and bent closed and the thread (34) is fixed to the bowel, and excess protruding bowel is cutoff circularly all the way around.

2. The instrument of claim 1, characterized in that the interchangeable insertion head (1) is embodied atraumatically in cross section, in the form of a cone (1a) with a rounded tip and a circular-annular shoulder (1b) with rounded transitions and contours.

3. The instrument of claim 1, characterized in that the largely circular-annular groove (33) has a number of notches corresponding to the number of staples (32) and is guided so as to intersect (at 33a) the outer circumference (30') of the staple holder.

4. The instrument of claim 1, characterized in that for secure holding of the bowel end on the mandrel (5), the gripper and holder arms (20) have hooklike shoulders (23) protruding inward from their distal ends.

5. The instrument of claim 1, characterized in that the annular knife (4), below its circular-linear blade (41) has a circular-annular collar (42) protruding radially into the interior of the knife, and that protrusions (21) each protruding radially outward are formed on the elastically resilient gripper and holder arms (20), so that upon the displacement of the mandrel (5) in the direction away from the joint (6), the gripper and holder arms (20) are pivoted radially outward and thereby opened.

6. The instrument of claim 1, characterized in that the mandrel (5), on its frustoconical distal end, has slits (52) for receiving a securing part (53) that locks into place and is provided in the insertion head (1).

7. The instrument of claim 1, characterized in that on the proximal end of the hollow gripper arm holder part (2), an annular shoulder (22) protruding into its interior is formed, and that the mandrel (5) on its proximal end has a groove (54) corresponding to the annular shoulder (22).

8. The instrument of claim 7 wherein the hollow shaft (7), the driving mechanism, the actuating wire (91), the tension wires, and the annular knife are made of high-alloy stainless steel or Al—Mn alloy; the joint (6) and the holder part (2) are made of viscoplastic plaster; the insertion head (1) is made of hard plastic, high-alloy stainless steel or Al—Mn alloy; and the staple holder (30), the mandrel (5), the handle (9) and the hand wheel (80) are made of hard plastic.

9. The instrument of claim 1, characterized in that the main portion of the joint body (61) is subdivided, by a number n (n=1, 2, 3, ... ) of notches (63), into a number of (n+1) segments (64), which are joined together by a remaining cross sectional region (62) to form a one-piece joint body (61); that for bending the joint (6) at an angle in the outer region of the segments (64), preferably diametrically opposed bores (65) aligned with one another are provided; and that at least one continuous conduit (66) is formed preferably concentrically and/or symmetrically to the center axis (6A) of the joint.

10. The instrument of claims 9, characterized in that the number n of notches (63) are made so deep into a circular-cylindrical block of material, beginning at two diametrically opposed jacket lines (61M, 61M'), both parallel and equidistant and at right angles and at an acute angle to the longitudinal axis (6a) of the block that for joining the (n+1) segments (64), a continuous, approximately rectangular, weblike remaining cross sectional region (62) remains between the facing ends of the two groups of notches (63a, 63b).

11. The instrument of claim 10 wherein the hollow shaft (7), the driving mechanism, the actuating wire (91), the tension wires, and the annular knife are made of high-alloy stainless steel or Al—Mn alloy; the joint (6) and the holder part (2) are made of viscoplastic plaster; the insertion head (1) is made of hard plastic, high-alloy stainless steel or Al—Mn alloy; and the staple holder (30), the mandrel (5), the handle (9) and the hand wheel (80) are made of hard plastic.

12. The instrument of claim 1, characterized in that to adjust and fix the joint (6) on the proximal end of the hollow shaft (7), an adjusting and fixing device (8) is provided, which has a clockwise- and counterclockwise- rotatable hand wheel (80) that is split in two and is lockable in a plurality of positions, whose shaft (81) is disposed at right angles to the longitudinal axis (7A) of the hollow shaft, and means, preferably wires, that exert tension can be secured to the grooved disk (81a) in order to bend, adjust and fix the joint (6).

13. The instrument of claim 12, characterized in that the handle (9) which is rotatable about its longitudinal axis (7A) together with the toggle lever mechanism (90) can be locked relative to the adjusting and fixing device (8) in a plurality of positions by means of a spring-loaded detent means, and the toggle lever mechanism (90, 93) is put in an open position by spring tension.

14. The instrument of claim 13, characterized in that the transmission ratio of the toggle lever mechanism (90), pivotably connected to the handle (9), is adapted to the requisite action path (s(a)) and course of motion of the functional elements, namely of the gripper and holder arms (20), of the annular knife (4), and of the ejector unit (35).

15. The instrument of claim 14 wherein the hollow shaft (7), the driving mechanism, the actuating wire (91), the tension wires, and the annular knife are made of high-alloy stainless steel or Al—Mn alloy; the joint (6) and the holder part (2) are made of viscoplastic plastic; the insertion head (1) is made of hard plastic, high-alloy stainless steel or Al—Mn alloy; and the staple holder (30), the mandrel (5), the handle (9) and the hand wheel (80) are made of hard plastic.

16. The instrument of claim 1, characterized in that the hollow shaft (7), the driving mechanism such as the actuating wire (91) and the tension wires, connecting elements, shafts, and the annular knife (4) are manufactured of high-alloy stainless steel, or X40Cr13.

17. The instrument of claim 1, characterized in that the insertion head (1), the hollow shaft (7), the driving mechanism including the actuating wire (91) and the tension wires, connecting elements, shafts, and the annular knife (4) are manufactured of selected hard-anodized aluminum materials, or aluminum-manganese (Al—Mn) alloys.

18. The instrument of claim 1, characterized in that the joint (6) and the holder part (2) having the gripper and holder arms (20) are made of viscoplastic plastic, or polytetrafluoroethylene (PTFE).

19. The instrument of claim 1, characterized in that the insertion head (1), the staple holder (30), the mandrel (5), the handle (9) and the hand wheel (80) are made of a harder plastic, such as polyoxymethylene (POM).

* * * * *